United States Patent [19]

Ward et al.

[11] Patent Number: 5,177,078

[45] Date of Patent: Jan. 5, 1993

[54] PIPERAZINE DERIVATIVES

[75] Inventors: Terence J. Ward, Reading; Graham J. Warrellow, Stanmore, both of England

[73] Assignee: John Wyeth & Brother Limited, Maidenhead, England

[21] Appl. No.: 768,147

[22] Filed: Sep. 30, 1991

[30] Foreign Application Priority Data

Oct. 3, 1990 [GB] United Kingdom ................ 9021453

[51] Int. Cl.$^5$ ................ A61K 31/495; A61K 31/535; A61K 31/55; C07D 403/00
[52] U.S. Cl. .................................... 514/253; 514/212; 514/252; 514/235.8; 540/598; 544/121; 544/295; 544/357; 544/360; 544/366; 544/367; 544/369; 544/370; 544/371; 544/372
[58] Field of Search ............... 544/121, 295, 357, 360, 544/366, 367, 369, 370, 371, 372; 540/598; 514/212, 252, 253, 235.8

[56] References Cited

U.S. PATENT DOCUMENTS 4,732,895 3/1988 Hofmann et al. .................... 544/364

FOREIGN PATENT DOCUMENTS 0395312 10/1990 European Pat. Off. .
2800535 7/1978 Fed. Rep. of Germany .

OTHER PUBLICATIONS

Von A. Kellmann et al.; Arzneimettel-Forschung, 31(8), 1178-83 (1981).
Sato et al., Chem. Pharm. Bull; 26(11), 3296-305 (1978).
J. B. Hester et al.; J. Med. Chem., 32(6), 1157-63 (1989).

Primary Examiner—Cecilia Tsang
Attorney, Agent, or Firm—Arthur G. Seifert

[57] ABSTRACT

Compounds of formula

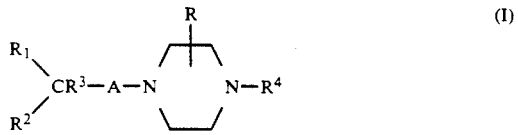

where A is an alkylene chain of 1 or 2 carbon atoms optionally substituted by one or more lower alkyl groups,
R is hydrogen or lower alkyl,
$R^1$ is an aryl or heteroaryl radical,
$R^2$ is a mono- or bicyclic heterocyclic radical,
$R^3$ is hydrogen, lower alkyl or hydroxy and
$R^4$ is a aryl or heteroaryl radical,
and their pharmaceutically acceptable acid addition salts are 5-HT$_{1A}$ binding agents which may be used, for example, for the treatment of CNS—disorders such as anxiety.

18 Claims, No Drawings

PIPERAZINE DERIVATIVES

This invention relates to piperazine derivatives, to processes for their preparation, to their use and to pharmaceutical compositions containing them. The novel compounds act upon the central nervous system by binding to 5-HT receptors (as more fully explained below) and hence can be used as medicaments for treating human and other mammals.

The novel compounds of the invention are those of the general formula

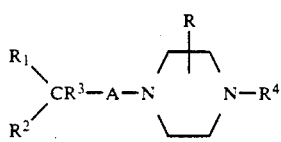 (I)

and the pharmaceutically acceptable acid addition salts thereof.

In formula (I):
A is an alkylene chain of 1 or 2 carbon atoms optionally substituted by one or more lower alkyl groups,
R is hydrogen or lower alkyl,
$R^1$ is an aryl or heteroaryl radical,
$R^2$ is a mono- or bicyclic heterocyclic radical,
$R^3$ is hydrogen or lower alkyl and
$R^4$ is a aryl or heteroaryl radical.

The term "lower" as used herein means that the radical referred to contains 1 to 6 carbon atoms. Preferably such radicals contain 1 to 4 carbon atoms. Examples of "lower alkyl" radicals are methyl, ethyl, propyl, isopropyl, butyl, isobutyl, tert-butyl, pentyl and isopentyl.

When used herein "aryl" means an aromatic radical having 6 to 12 carbon atoms (e.g. phenyl or naphthyl) which optionally may be substituted by one or more substituents. For example, when $R^1$ is aryl it may be a phenyl or naphthyl radical optionally substituted by one or more lower alkyl, lower alkoxy (e.g. methoxy, ethoxy, n or i-propoxy, butoxy, cyclopropylmethoxy), halogen, halo(lower)alkyl (e.g. trifluoromethyl), nitro, amino, (lower)alkylamino, di(lower)alkylamino, phenyl, halophenyl, (lower)alkylphenyl or (lower)alkoxyphenyl substituents. When $R^4$ is aryl it may be, for example, a phenyl or naphthyl radical optionally substituted by one or more of the substituents listed above and/or by one or more hydroxy, hydroxy(lower)alkyl (e.g. hydroxymethyl), $-CONR^5R^6$ (where $R^5$ and $R^6$ are each hydrogen or lower alkyl) or $-NHSO_2$(lower)alkyl substituents. Preferably the aryl radical $R^4$ contains a substituent (e.g. lower alkoxy) in the ortho position. A particularly preferred example of $R^4$ is o-(lower)alkoxyphenyl (e.g. o-methoxyphenyl).

The term "heteroaryl" refers to an aromatic radical containing one or more hetero ring atoms (e.g. oxygen, nitrogen, sulphur) and which may be optionally substituted by one or more substituents. Preferred examples of substituents for the heteroaryl radical $R^1$ are given above for the aryl radical $R^1$ while preferred examples of substituents for the heteroaryl radical $R^4$ are given above for the aryl radical $R^4$. The heteroaryl radical may be, for example, mono- or bicyclic containing up to 11 ring atoms. The heteroaryl radical may, for example be a monocyclic radical containing 5 to 7 ring atoms or a bicyclic radical containing 9 to 11 ring atoms. Preferably the hetero ring contains a nitrogen hetero atom with or without further hetero atoms. Examples of the heteroaryl group $R^1$ are optionally substituted pyridinyl, pyrimidinyl, pyrazinyl, imidazolyl, pyrazolyl, triazolyl, benzimidazolyl and oxadiazolyl tetrazolyl and oxadiazolyl. These groups may be connected to the remainder of the molecule via a ring heteroatom or a ring C atom. Examples of the heteroaryl group $R^4$ include optionally substituted pyridinyl, pyrimidinyl, pyrazinyl, quinolinyl and isoquinolinyl.

$R^2$ is a mono- or bicyclic heterocyclic radical. The radical may be heteroaryl radical such as those mentioned above including the preferred examples given in connection with radical $R^1$. In addition $R^2$ may be fully or partially saturated mono- or bicyclic heterocyclic ring. The mono or bicyclic ring contains one or more hetero ring atoms (e.g. oxygen, nitrogen and/or sulphur) and may be optionally substituted by one or more substituents (such as those given above for the group $R^1$). The mono or bicyclic ring preferably contains up to 10 carbon atoms. Examples include optionally substituted imidazolinyl, oxazolinyl, pyrrolidinyl, piperidinyl, morpholinyl and azepinyl.

Examples of the radical —A— include $-CH_2-$, $-CHCH_3-$, $-C(CH_3)_2-$, $-CH_2-CH_2-$, $-CH_2-CH(CH_3)-$, $-CH(CH_3)\cdot CH(CH_3)-$ and $-CH_2-C(CH_3)_2-$.

Preferred compounds have the following substituents either independently or in combination:
(a) A is $CH_2$
(b) $R^1$ is aryl, preferably phenyl
(c) $R^2$ is 1H imidazol-1-yl
(d) $R^3$ is hydrogen
(e) $R^4$ is aryl
(f) R is hydrogen The compounds of the invention may be prepared by methods known in the art from known starting materials or starting materials that may be prepared by conventional methods.

One method of preparing the compounds of the invention comprises alkylating a piperazine derivative of formula

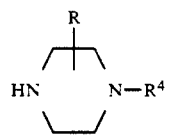 (II)

with an alkylating agent providing the group

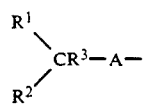 (III)

The alkylating agent may be, for example, a compound of formula

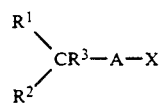 (IV)

where $R^1$, $R^2$, $R^3$ and A are as defined above and X is a leaving group such as halogen or an alkyl— or aryl-sulphonyloxy group. Alternatively the alkylating agent may be an unsaturated compound of formula

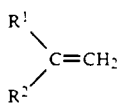
(V)

(where at least one of the groups R¹ and R² is an electron withdrawing group e.g. an optionally substituted 2- or 4- pyridyl, 2- or 4- pyrimidyl or 2-pyrazinyl group) and the compound of formula (V) is reacted with the piperazine compound of formula (II) by means of a Michael reaction.

The compounds of formula (I) may also be prepared by reduction of an amide of formula

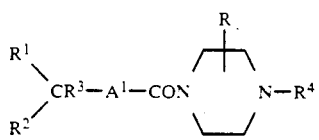
(VI)

where R, R¹, R², R³ and R⁴ are as defined above and A¹ is methylene optionally substituted by one or two (lower)alkyl groups. The reduction may, for example, be carried out with a hydride transfer agent e.g. borane-dimethylsulphide or lithium aluminium hydride. The starting amide of formula (VI) may be made by acylating a piperazine derivative of formula (II) above with an acylating derivative of an acid of formula

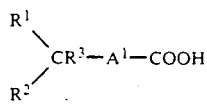
(VII)

The acylating derivative may be, for example, the acid chloride.

Compounds of the invention in which R¹ or R² is a heterocyclic radical attached via a ring N-atom may be prepared by reacting a heterocyclic compound of formula R¹H or R²H e.g. imidazole with, respectively a compound of formula

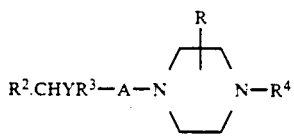
(VIIIa)

or

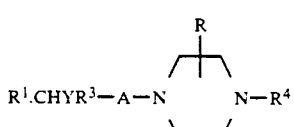
(VIIIb)

where R, R¹, R², R³, R⁴ and A are as defined above, and Y is a leaving group such as halogen or an alkyl- or arylsulphonyloxy group.

An alternative method of preparing the compounds of the invention comprises arylating or heteroarylating a compound of formula

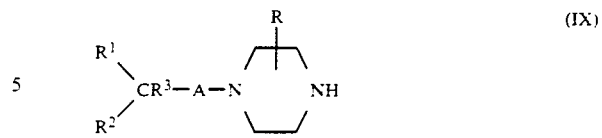
(IX)

For example the compound of formula (IX) may be reacted with a fluorobenzene compound which is substituted by an electron withdrawing group (e.g. —CHO, cyano, nitro).

Another method of preparing the compounds of the invention comprises reacting a compound having the anion

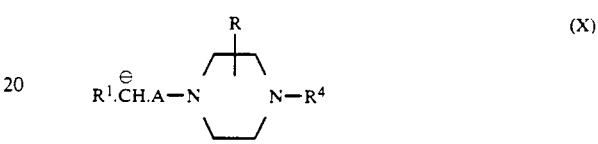
(X)

with a compound of formula

R²X          (XI)

where X is a leaving group which is activated towards nucleophilic displacement. For example R² can be an electron withdrawing radical (e.g. an optionally substituted 2- or 4-pyridyl, 2- or 4-pyrimidyl or 2-pyrazinyl group) and X a leaving group such as fluorine. The radical R¹ is also, preferably an electron withdrawing group. The anion (X) may be prepared by reacting the compound

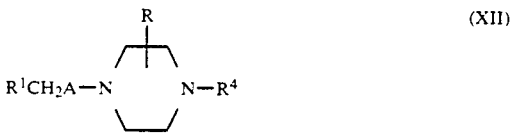
(XII)

with a base e.g. n-butyl lithium.

Compounds of the invention may also be prepared by forming an anion of a compound of formula

(XIII)

(e.g. with a strong base) and reacting with a compound of formula

(XIV)

where A, R, R¹, R², R³ and R⁴ are as defined above and Y is a leaving group such as halogen or an alkyl— or aryl-sulphonyloxy group.

In a further method of preparing the compounds of the invention a compound of formula

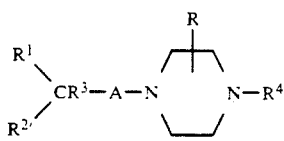

(XV)

in which R, R¹, R³, R⁴ and A are as defined above and R²' is an uncyclised group which is a precursor of a mono or bicyclic heterocyclic radical is cyclised to the compound of the invention. The cyclisation may be carried out by methods known per se. For example R²' may be an alkoxycarbonyl group which may be cyclised by reaction an amidoxime (eg acetamidoxime) to give a compound in which R² is a 1,2,4-oxidiazol-5-yl radical.

If in any of the other processes mentioned herein, a substituent on the group R⁴ or on the group R¹ and/or R² is other than the one required the substituent may be converted to the desired substituent by known methods For example, a —CHO substituent may be reduced to hydroxymethyl, a nitro group may be reduced to a amino group which may be sulphonated to give a —NHSO₂(lower)alkyl substituent, a cyano group may be hydrolysed to an acid which may be esterified or converted to an amide. Furthermore one heterocyclic group, R¹ and R² may be converted into another heterocyclic group by methods known per se.

The processes described above may be carried out to give a compound of the invention in the form of a free base or as an acid addition salt. If the compound of the invention is obtained as an acid addition salt, the free base can be obtained by basifying a solution of the acid addition salt. Conversely, if the product of the process is a free base an acid addition salt, particularly a pharmaceutically acceptable acid addition salt, may be obtained by dissolving the free base in a suitable organic solvent and treating the solution with an acid, in accordance with conventional procedures for preparing acid addition salts from base compounds.

Examples of acid addition salts are those formed from inorganic and organic acids, such as sulphuric, hydrochloric, hydrobromic, phosphoric, tartaric, fumaric, maleic, citric, acetic, formic, methanesulphonic, p-toluenesulphonic, oxalic and succinic acids.

The compounds of the invention may contain an asymmetric carbon atom, so that the compounds can exist in different steroisomeric forms. The compounds can be for example, racemates or optically active forms. The optically active forms can be obtained by resolution of the racemates or by asymmetric synthesis.

The compounds of the present invention possess pharmacological activity. In particular, they act on the central nervous system by binding to 5-HT receptors. In pharmacological testing it has been shown that the compounds particularly bind to receptors of the 5-HT$_{1A}$ type In general, the compounds selectively bind to receptors of the 5-HT$_{1A}$ type. Many exhibit activity as 5-HT$_{1A}$ antagonists in pharmacological testing. The pharmacological testing of the compounds indicates that they can be used for the treatment of neuro-psychiatric disorders, such as anxiety and depression in mammals, particularly humans. They may also be useful as hypotensives and as agents for regulating the sleep-/wake cycle, feeding behaviour and/or sexual function.

The compounds of the invention are tested for 5-HT$_{1A}$ receptor binding activity in rat hippocampal membrane homogenate by the method of B S Alexander and M D Wood, J Pharm Pharmacol, 1988, 40, 888–891. (R,S)-1-(2-Methoxyphenyl) -4-[2-(IH-imidazol-1-yl)-2 (phenyl) ethyl]piperazine, a representative compound of the invention had an IC$_{50}$ of 15.8nM in this procedure.

The compounds are tested for 5-HT$_{1A}$ receptor antagonism activity in a test involving the antagonism of 8-hydroxy-2-(di-n-propylamino)-tetralin (8-OH DPAT) syndrome in the rat. (R,S)-1-(2-Methoxyphenyl)-4-[2-(IH-imidazol-1-yl) -2-(phenyl)ethylpiperazine had MED of 1 mg/kg subcut and 10 mg/kg p.o when tested in this procedure.

The invention also provides a pharmaceutical composition comprising a compound or a pharmaceutically acceptable acid addition salt thereof in association with a pharmaceutically acceptable carrier. Any suitable carrier known in the art can be used to prepare the pharmaceutical composition. In such a composition, the carrier is generally a solid or liquid or a mixture of a solid or liquid.

Solid form compositions include powders, granules, tablets, capsules (e.g. hard and soft gelatine capsules), suppositories and pessaries. A solid carrier can be, for example, one or more substances which may also act as flavouring agents, lubricants, solubilisers, suspending agents, fillers, glidants, compression aides, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%. preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilisers, emulsifiers, buffers, preservatives, sweetners, flavouring agents, suspending agents, thickening agents, colours, viscosity regulators, stabilisers or osmo-regulators. Suitable examples of liquid carriers for oral and parenteral administration include water (particularly containing additives as above, e.g. cellulose derivatives, preferably sodium carboxymethyl cellulose solution, alcohols, e.g. glycerol and glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intrapertioneal or subcutaneous injection. Sterile solutions can also be administered intravenously. When the compound is orally active it can be administered orally either in liquid or solid composition form.

Preferably the pharmaceutical composition is in unit dosage form e.g. as tablets or capsules. In such form, the composition is sub-divided in unit dose containing appropriate quantities of the active ingredient; the unit dosage forms can be packaged composition, for example packeted powders, vials, ampoules, prefilled syringes or sachets containing liquid. The unit dosage form can be, for example, a capsule or tablet itself, or it can be the appropriate number of any such compositions in package form. The quantity of the active ingredient in unit dose of composition may be varied or adjusted from 0.5 mg or less to 750 mg or more, according to the particular need and the activity of the active ingredient.

The following Examples illustrate the invention:

EXAMPLE 1

1-(2-Methoxyphenyl)-4-[2-1H-imidazol-1-yl)-2-(phenyl)ethyl]piperazine (a) 1-(2-Hydroxy-2-phenylethyl)-4-(2-methoxyphenyl) piperazine 1-(o-Methoxyphenyl)piperazine (25g) in acetonitrile (250 ml) was added dropwise to a solution of styrene oxide (14.92 ml) in acetonitrile (150 ml) at room temperature. The reaction mixture was stirred overnight, refluxed for 28 hours and allowed to stand overnight. The solvent was removed and the residue dissolved in ether and washed with water. The ether layer was evaporated to give the crude title compound (ca 40 g).

(b)
1-(2-Methoxyphenyl)-4-[2-(1H-imidazol-1-yl)-2-(phenyl)ethyl]piperazine

A mixture of 1-(2-hydroxy-2-phenylethyl)-4-(2-methoxyphenyl) piperazine hydrochloride (1.6 g) and thionyl chloride (5 ml) was stirred at reflux for 5 min. The clear solution was then diluted with ether and the precipitated product collected by filtration and washed well with ether. The solid was added to a solution of imidazole (2.4 g, 40 mmol) in methanol (20 ml) and heated to reflux for 1 h. The reaction mixture was diluted with water and extracted with ethyl acetate. The extract was washed several times with water, dried (Na$_2$SO$_4$), and concentrated in vacuo. The residue was dissolved in ethanol (10 ml) and acidified with ethereal-HCl. Further addition of ether precipitated the hydrochloride (1.07 g, 55%), which was recrystallised from methanol-ethanol (20 ml; 1:3) to afford the title compound as the trihydrochloride 1.25 hydrate (0.54 g), m.p. 203°-204° C. (Found: C,53.2; H,6.4; N,11.2. C$_{22}$H$_{26}$N$_4$O.3HCl$_{1.1.25}$H$_2$O requires C,53.4; H,6.4; N,11.3%).

EXAMPLE 2

1-(2-Methoxyphenyl)-4-[2-(2-Methyl-[1H]imidazol-1-yl)-2-phenyl)ethyl]piperazine

To a mixture of 1-(2-hydroxy-2-phenylethyl)-4-(2-methoxyphenyl)-piperazine (5.67 g; 0.02 m); triphenylphosphine (5.69 g; 0.0217 m) and 2-methylimidazole (16 g; 0.195m) in dichloromethane (150 ml) was added diethylazodicarboxylate (3.82 ml; 0.024 m) in dichloromethane (10 ml) over 10 minutes at ambient temperature. After the initial exotherm subsided, the mixture was stirred for 3 days. The residue on evaporation was treated with 3N HCl. Ether was added and the resulting two layers separated. The ether layer was washed twice with 3N HCl. The combined HCl layers were basified with ammonia and then shaken with ether (3 portions). The ether layers were washed well with water. The final ether layer was dried over magnesium sulfate. The oil on evaporation was dissolved in hot ethanol and acidified with ethanolic HCl. The solvent was evaporated to leave a foam that solidified when triturated with ether. A little ethanol was added and the solid filtered off. The mother liquor yielded 0.67 g of product which was recrystallised from ethanol to give the title compound as the trihydrochloride, m.p. >177° C. Found: C,54.45; H,6.69; N,10.92%. C$_{23}$H$_{28}$N$_4$O.3HCl.H$_2$O requires C,54.82; H,6.6; N,11.12%.

EXAMPLE 3

1-(2-Methoxyphenyl)-4-[2-(1-pyrrolidinyl)-2-(phenyl)ethyl]piperazine

A mixture of 1-(2-hydroxy-2-phenylethyl)-4-(2-methoxyphenyl)-piperazine (5.65 g; 0.018 m), triphenylphosphine (5.69 g, 0.022m) and pyrollidine (15 ml; 0.18 m) in dichloromethane (100 ml) was stirred at 0.5° C. and a solution of diethylazodicarboxylate (3.8 ml, 0.024 m) in dichloromethane (5 ml) was added over 5 minutes. The resulting yellow solution was stirred at ambient temperature for 48 hrs. The residue on evaporation was partitioned between ether and 3N aq. hydrochloric acid. The combined HCl layers were washed with ether and then basified with ammonia and shaken with 3 portions of ether. The ether layers were washed well with water and dried over magnesium sulfate to give an oil which was chromatographed to give 0.96 g of the title compound. The crude oil in ethanol was acidified with ethanolic hydrogen chloride. The solvent was evaporated, and the residual foam solidified when triturated with ethanol and ether. The solid was recrystallised from ethanol to give the title compound as the dihydrochloride (0.45 g), m.p. 214°-18° C(d).

EXAMPLE 4

1-(2-Methoxyphenyl)-4-[2-(1H-imidazol-1-yl)-2-(4-fluorophenyl)ethyl]piperazine

Thionyl chloride (1.25 g, 0.82 ml) was added dropwise to a stirred solution of 1-[2-hydroxy-2-(4-fluorophenyl]-4-(2-methoxyphenyl)-piperazine (2.31 g, 7 mmol) in DMF (15 ml) maintained below 15° C. by ice-cooling. The solution was allowed to stand at ambient temperature for 0.5 h and imidazole (4.76 g, 70 mmol) added. The mixture was heated at 80° C. for 1.5 h, then cooled, diluted with water and extracted into ethyl acetate. The extract was washed with water, dried over Na$_2$SO$_4$ and evaporated. The residue was dissolved in ethanol (15 ml) and acidified with ethereal-HCl to precipitate the title compound as the hydrochloride (1.58 g), m.p. 242°-243° C.

EXAMPLE 5

(a)
1-(2-Methoxyphenyl)-4-[2-phenyl-2-(1H-benzimidazol-1-yl)-1-oxoethyl]piperazine A mixture of sodium hydride (0.47 g of 80% dispersion) in dry dimethyl formamide (10 ml) at 0°-5° C. was treated with benzimidazole (1.584 g) and the mixture stirred for 30 mins. A solution of 1-(2-methoxyphenyl)-4-(2-chloro-1-oxo-2-phenylethyl) piperazine (4.624 g) in dry DMF (20 ml) was added and the mixture was stirred at 90° C. for 5 hrs then at ambient temperature overnight. The suspension was filtered and the solvent evaporated under vacuum. The residue, in dichloromethane was washed well with water and dried over magnesium sulphate, to give 6 g of an oil. The crude product was purified by dry column flash chromatography to give the title compound (2.4 g).

(b) 1-(2-methoxyphenyl)-4-[2-1-yl)-2-phenylethyl]piperazine.

1-(2-methoxyphenyl)-4-[2-phenyl-2-(1H-benzimidazol-1-yl)-1-oxoethyl]piperazine (9.4 g) in 50 ml dry tetrahydrofuran was treated with borane-dimethylsulphide in THF (100ml of 2.0 M solution) over 30 mins and then heated to reflux. After 3 hrs at reflux following by overnight stirring at ambient temperature the mixture was cooled to 0°–5° C. Concentrated hydrochloric acid (50 ml) was added over 30 mins and the mix was stirred at 90° C. for 1½ hrs, then at ambient temperature for 4 hrs. The mixture was filtered and the filtrate was evaporated, the residue partitioned between water and diethylether and the aqueous layer extracted with ether. The ether layers were washed with water and evaporated to give a solid that recrystallised from cyclohexane to give title compound (3.85 g) which was converted to its hydrochloride. m.p. 196°–201° C.

EXAMPLE 6

1-(2-Methoxyphenyl)-4-[2-phenyl-2-(4-phenyl-1H-imidazol-1-yl)ethyl]piperazine 2.0 M Borane-methylsulphide in THF (45 ml) was added over 45 mins to a solution of 1-(2-methoxyphenyl)-4-[1-oxo-2-phenyl-2-(4-phenyl-1H-imid azol-1-yl) ethyl]piperazine (4.0 g, 0.009 m, prepared in an analogous manner to the method of Example 5a) in dry THF (30 ml) at ambient temperature, and the mixture was then refluxed 24 hrs. The cooled mixture was treated with conc. HCl (25 ml) dropwise over 30 mins and the resulting white suspension was then heated at 90° C. for 4 hrs. After further standing 48 hrs the mixture was filtered. The white solid was washed with 6N HCl and dried, then recrystallised from ethanol to yield the title compound as the trihydrochloride (1.425 g), m.p. 233°–36° C.(d).

EXAMPLE 7

(R)-[1-(2-Methoxyphenyl)-4-(2-phenyl-2-hydroxyethyl)piperazine]

2-Methoxyphenylpiperazine (19.84 g, 0.103 m) in dry acetonitrile (150 ml) was refluxed with (R)-styrene oxide (12.4 g, 0.104 m). The residue on evaporation was chromatographed on silica using ethyl acetate as eluant to give two main fractions. The first fraction (4.3 g) contained some styrene oxide, which was removed by acid-base extraction to give 3.55 g of pure title compound. The second fraction (9.5 g) was 95% title compound and approximately 5% of the regioisomer.

(S)-[1-(2-Methoxyphenyl)-4-(2-(1H-imidazol-1-yl)-2-phenylethyl) piperazine].

The above pure isomer (3.55 g, 0.0114 m) was mixed in dichloromethane (100 ml) with triphenylphosphine (3.59 g, 0.014 m) and imidazole (9 g, 0.132 m). The solution was treated over 8 minutes with diethylazodicarboxylate (2.6 ml) in dichloromethane. The solution was stirred at ambient temperature for 3 days and then evaporated.

The residue was dissolved in diethylether (150 ml) and washed with water. The ether layer was then shaken with 6N HCl (3×100 ml). The combined HCl layers were washed with ether. The HCl layers were cooled and basified with 0.880 ammonia, and shaken with ether (3×100 ml). The ether extracts were washed with water and dried over magnesium sulphate, to give 6.7 g of an oil. The oil was dissolved in ethanol (150 ml) at 70° C. and acidified in ethanolic HCl. The solid which precipitated on cooling was filtered off to give the trihydrochloride monohydrate, m.p. 193°–197° C., $[\alpha]^{23}_D -27°$.

EXAMPLE 8

(S)-[1-(2-Methoxyphenyl)-4-(2-phenyl-2-hydroxyethyl)piperazine]

2-Methoxyphenylpiperazine (17.4 g, 0.0906 m) in dry acetonitrile (150 ml) was refluxed 24 hrs with (S)-styrene oxide (10.84 g, 0.09 m). The residue on evaporation was treated by acid-base extraction to remove unreacted styrene oxide to leave 28 g of the crude alcohol as a mixture of regioisomers which was purified by chromatography on silica, using 1:1 hexane ethylacetate, to give 16.5 g of the pure isomer, $[\alpha]^{23}_D +56°$ C.

(R)-[1-(2-Methoxyphenyl)-4-(2-(1H-imidazol-1-yl)-2-phenelethyl)piperazine]

The above pure isomer (5.15 g, 0.0165m) was mixed in dichloromethane (100 ml) with triphenylphosphine (5.21 g, 0.02m) and imidazole (13 g, 0.2 m). The solution was treated over 10 mins with diethylazodicarboxylate (3.8 ml) in dichloromethane (5 ml). The solution was stirred 3 days at ambient temperature and then evaporated. The residue was dissolved in ether (200 ml) and washed with water. The ether layer was then shaken with 6N HCl (3×100 ml). The combined HCl layers were shaken with ether. The HCl layer was cooled, and basified with 0.880 ammonia, and then shaken with ether. The ether extracts were washed with water and dried over magnesium sulphate, to give 6.8 g of an oil. This was dissolved in hot ethanol, acidified (EtOH-HCl), recrystallised from hot ethanol to give the title compound as the trihydrochloride monohydrate, m.p. 192°–195°, $[\alpha]23 +27°$.

EXAMPLE 9

1-(2-Methoxyphenyl)-4-[3-(1H-imidazol-1-yl)-3-phenyl)propyl]piperazine

Thionyl chloride (0.88 ml) was added dropwise to an ice-cooled solution of 1-(2-methoxyphenyl)-4-(3-hydroxy-3-phenyl) piperazine (2.45 g 7.5 mmol) in dry DMF (15 ml). The solution was allowed to stand for 0.5 h and then imidazole (5.1 g, 75 mmol) added in one portion. The mixture was heated at 80° C. for 1.5 h, diluted with water and extracted with ethyl acetate. The extract was dried ($Na_2SO_4$), evaporated and the residue chromatographed on silica using 5% methanol in chloroform as eluent to give the product as an oil (0.55 g). The base was dissolved in ethanol (5 ml), acidified with ethanolic —HBr and diluted with ether (3 ml) to precipitate the title compound as the trihydrobromide 0.46 g, m.p. 224-226° C.

EXAMPLE 10

1-(2-Methoxyphenyl)-4-[2-(4-methyl-1H-imidazol-1-yl)-2-phenyl) ethyl]piperazine

The title compound was prepared following the procedure of Example 2 using 4-methylimidazole instead of 2-methylimidazole. The product was converted to its trihydrochloride monohydrate, m.p. 200°–205° C. (Found C, 54.5; H, 6.48; N, 11.04% $C_{23}H_{28}N_4O.3HCl.H_2O$ requires C, 54.82; H, 6.60; N, 11.12%).

EXAMPLE 11

5-(3-(4-(2-Methoxyphenyl)piperazin-1-yl)1-phenyl-propyl)-3-methyl-1,2,4-oxadiazole A solution of acetamidoxime (0.65 g, 8.7 mmol) in tetrahydrofuran (20 ml) added to a stirred suspension of sodium hydride (0.35 g, 60% dispersion in oil, 8.7 mmol) in tetrahydrofuran (10 ml). The reaction mixture was heated under reflux for 1 h and a solution of methyl 4-(4-(2-methoxyphenyl)piperazin-1-yl)-2-phenylbutanoate (2.68 g, 7.3 mmol) in tetrahydrofuran (30 ml) was added dropwise. The reaction mixture was heated under reflux for a further 2 h. The cooled reaction mixture was treated with water (80 ml) and the solvent removed under reduced pressure. The aqueous residue was washed with ethyl acetate and the combined organic phases washed with water. The organic phase was dried ($MgSO_4$), concentrated and chromatographed on silica gel, eluting with ethyl acetate:hexane (2:1) to afford an oil. The oil was dissolved in acetonitrile and acidified with ethereal hydrogen chloride to give the title compound as the dihydrochloride, colourless crystals, m.p. 189.5°–191.8° C.

EXAMPLE 12

5-[2-(4-(2-Methoxyphenyl)piperazin-1-yl)-1-phenylethyl]-3-methyl-1,2,4-oxadiazole A solution of acetamidoxime (0.90 g, 12.1 mmol) in tetrahydrofuran (50 ml) was added to sodium hydride (0.74 g, 60% dispersion in oil, (11.1 mmol) in tetrahydrofuran (10 ml). The reaction mixture was then heated under reflux for 1 h and a solution of methyl 3-(4-(2-methoxyphenyl)piperazin-1-yl)-2-phenylpropanote (3.58 g, 10.1 mmol) in tetrahydrofuran (50 ml) was added. The reaction mixture was heated under reflux for 0.5 h, allowed to cool and then poured into water (100 ml). The tetrahydrofuran was removed under reduced pressure and the aqueous residue washed with ethyl acetate. The combined organic phases were washed with water, dried ($MgSO_4$) and concentrated to afford a yellow oil (2.12 g). The oil was chromatographed on silica gel, eluting with ethyl acetate:hexane (1:1) to afford a pale yellow solid (1.40 g). The solid (0.50 g) was dissolved in ethyl acetate and a solution of maleic acid (0.153 g) in ethyl acetate added to afford the title compound as the maleate (0.39 g), m.p. 151.2° to 151.6° C.

We claim:
1. A compound of the formula

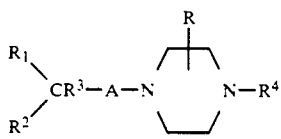

(I)

wherein
A is $-CH_2-$, $-CHCH_3-$, $-C(CH_3)_2$, $-CH_2CH_2-$, $CH_2-CH(CH_3)-$, $CH(CH_3-CH(CH_3)-$, and $-CH_2-C(CH_3)_2-$, R is hydrogen or lower alkyl, $R^1$ is an aryl or a mono- or bicyclic heteroaryl radical of from 5 to 11 ring atoms having one or two hetero atoms independently selected from N, O or S, or having three or four N atoms, which may be optionally substituted as for aryl, $R^2$ is a mono- or bicyclic heterocyclic radical of from 5 to 11 ring atoms having one or two hetero atoms selected from N, O or S which may be optionally substituted as for aryl, $R^3$ is hydrogen or lower alkyl, and $R^4$ is aryl or a mono- or bicyclic heteroaryl radical of from 5 to 11 ring atoms having one or two hetero atoms selected from N, O or S which may be optionally substituted as for aryl, wherein aryl refers to an aromatic radical having 6 to 12 carbon atoms which may be optionally substituted by one to three substituents selected from lower alkyl, lower alkoxy halogen halo(lower)akyl, nitro, amino, mono- or di-(lower)alkylamino.

2. A compound as claimed in claim 1 in which A is $-CH_2-$ or $-CH_2CH_2-$.

3. A compound as claimed in claim 1 in which $R^1$ is a phenyl or naphthyl radical optionally substituted by one or more lower alkyl, lower alkoxy, halogen, halo(lower)alkyl, nitro, amino, lower(alkyl)amino, di(lower)alkylamino, phenyl, halophenyl, (lower)alkylphenyl or (lower)alkoxyphenyl substituents.

4. A compound as claimed in any one of claims 1 to 3 in which $R^2$ is optionally substituted pyridinyl, pyrimidinyl, pyrazinyl, imidazolyl, pyrazolyl, triazolyl, benzimidazolyl, oxadiazolyl, imidazolinyl, oxazolinyl, pyrrolidinyl, piperidinyl, morpholinyl or azepinyl.

5. A compound as claimed in claim 1 which is 1-(2-methoxyphenyl)-4-[2-1H-imidazol-1-yl)-2(phenyl)ethyl]piperazine or a pharmaceutically acceptable acid addition salt thereof.

6. A compound as claimed in claim 1 which is 1-(2-methoxyphenyl)-4-[2-(2-methyl-[1H]imidazol-1-yl)-2-phenyl)ethyl]piperazine or a pharmaceutically acceptable acid addition salt thereof.

7. A compound as claimed in claim 1 which is 1-(2-methoxyphenyl)-4-[2-(1-pyrrolidinyl)-2-(phenyl)ethyl]-piperazine or a pharmaceutically acceptable acid addition salt thereof.

8. A compound as claimed in claim 1 which is 1-(2-methoxyphenyl)-4-[2-(1H-imidazol-2-(4-fluorophenyl)ethyl]piperazine or a pharmaceutically acceptable acid addition salt thereof.

9. A compound as claimed in claim 1 which is 1-(2-methoxyphenyl)-4-[2-phenyl-2-(4-phenyl-1H-imidazol-1-yl)ethyl]piperazine or a pharmaceutically acceptable acid addition salt thereof.

10. A compound as claimed in claim 1 which is 1-(2-methoxyphenyl)-4-[2-(1H-benzimadol-1-yl)-2-phenylethyl]piperazine or a pharmaceutically acceptable acid addition salt thereof.

11. A compound as claimed in claim 1 which is (S)-[1-(2-methoxyphenyl)-4-(2-(1H-imidazol-1-yl)-2-phenylethyl)piperazine or a pharmaceutically acceptable acid addition salt thereof.

12. A compound as claimed in claim 1 which is (R)-[1-(2-methoxyphenyl)-4-[2-(1H-imidazol-1-yl)-2- phenylethyl]piperazine or a pharmaceutically acceptable acid addition salt thereof.

13. A compound as claimed in claim 1 which is 1-(2-methoxyphenyl)-4-[3-(1H-imidazol-1-yl)-3-phenyl)-propyl]piperazine or a pharmaceutically acceptable acid addition salt thereof.

14. A compound as claimed in claim 1 which is 1-(2-methoxyphenyl)-4-[2-(4-methyl-1H-imidazol-1-yl)-2-phenyl)ethyl]piperazine or a pharmaceutically acceptable acid addition salt thereof.

15. A compound as claimed in claim 1 which is 5-(3-(4-(2-methoxyphenyl)piperazin-1-yl)-1-phenylpropyl)-3-methyl-1,2,4-oxadiazole or a pharmaceutically acceptable acid addition salt thereof.

16. A compound as claimed in claim 1 which is 5-[2-(4-(2-methoxyphenyl)piperazin-1-yl)-1-phenylethyl]-3-methyl-1,2,4-oxadiazole.

17. A pharmaceutical composition for treating anxiety or depression comprising an amount of a compound claimed in claim 1 effective to alleviate anxiety or depression in association with a pharmaceutically acceptable carrier.

18. A method of treating anxiety or depression in a mammal, which comprises administering to said mammal an amount of a compound of claim 1 effective to alleviate anxiety or depression.

* * * * *